US011581071B2

(12) United States Patent
Birrer et al.

(10) Patent No.: US 11,581,071 B2
(45) Date of Patent: Feb. 14, 2023

(54) LABORATORY SYSTEM FOR ANALYZING BIOLOGICAL SAMPLES

(71) Applicant: Roche Diagnostics Operations, Inc., Indianapolis, IN (US)

(72) Inventors: Armin Birrer, Udligenswil (CH); Marco Maetzler, Belmont, CA (US); André Peter, Meggen (CH); Ole Lambaek, Cham (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 725 days.

(21) Appl. No.: 16/545,735

(22) Filed: Aug. 20, 2019

(65) Prior Publication Data
US 2020/0075137 A1    Mar. 5, 2020

(30) Foreign Application Priority Data

Aug. 29, 2018    (EP) .................................... 18191546

(51) Int. Cl.
*G06Q 10/00*    (2012.01)
*G16H 10/40*    (2018.01)
(Continued)

(52) U.S. Cl.
CPC ....... *G16H 10/40* (2018.01); *G01N 35/00732* (2013.01); *G06F 16/2365* (2019.01); (Continued)

(58) Field of Classification Search
CPC ........ G16H 10/40; G16H 10/60; G16H 70/20; G01N 35/0092; G01N 35/00732; G01N 2035/0094; G01N 2035/00831; G01N 35/0095; G01N 2035/009; G01N 2035/00881; G01N 2035/00851; G01N 35/00871; G01N 2035/00752; G01N 35/00722; G01N 2035/0401; G01N 35/00613; G01N 35/00623;
(Continued)

(56) References Cited

U.S. PATENT DOCUMENTS 5,871,697 A * 2/1999 Rothberg ............. C12Q 1/6809
                                                    435/6.12
6,432,673 B1 * 8/2002 Gao ....................... C07K 14/52
                                                    435/325
(Continued)

FOREIGN PATENT DOCUMENTS

EP         3182133 A1    6/2017

OTHER PUBLICATIONS

European Search Report dated Feb. 21, 2019, in Application No. 18191546.3, 2 pp.

*Primary Examiner* — Thien M Le
(74) *Attorney, Agent, or Firm* — Roche Diagnostics Operations, Inc.

(57) ABSTRACT

A laboratory system for analyzing biological samples is presented. The laboratory system comprises a plurality of laboratory instruments configured to receive and identify biological samples and to query a laboratory control unit for a processing order indicative of processing steps to be carried out on the biological sample. The laboratory control unit is configured to validate sequence of queries from the plurality of laboratory instruments against a valid query sequence pattern.

15 Claims, 6 Drawing Sheets

(51) Int. Cl.
  *G01N 35/00* (2006.01)
  *G06F 16/245* (2019.01)
  *G06F 16/23* (2019.01)
  *G16H 10/60* (2018.01)

(52) U.S. Cl.
  CPC ...... *G06F 16/245* (2019.01); *B01L 2300/021* (2013.01); *G01N 2035/009* (2013.01); *G01N 2035/00752* (2013.01); *G01N 2035/00831* (2013.01); *G01N 2035/00851* (2013.01); *G16H 10/60* (2018.01)

(58) Field of Classification Search
  CPC ..... G01N 35/1016; G01N 2035/00227; G01N 2035/00633; G01N 2035/00841; G01N 33/483; G01N 35/00584; G01N 35/026; G01N 35/02; G01N 2001/2893; G01N 2035/00891; G01N 2035/0096; G01N 2035/0498; G01N 2035/1032; G01N 35/00663; G01N 35/00712; G01N 35/04; G01N 2035/00673; G01N 2035/00653; G01N 2035/00742; G01N 35/00693; G01N 35/0099; B01L 2200/14; B01L 3/021; B01L 2300/021; B01L 99/00; G06F 16/2365; G06F 16/245; G05B 19/0423; G05B 2219/24215; G06K 17/0022; B65G 1/1371; G06Q 10/08; G06Q 10/087; G06Q 50/28
  See application file for complete search history.

(56) References Cited

U.S. PATENT DOCUMENTS

| | | | | |
|---|---|---|---|---|
| 6,927,779 | B2* | 8/2005 | Mannion | G06T 11/206 345/650 |
| 7,157,619 | B1* | 1/2007 | Lassner | C12N 15/8247 536/23.6 |
| 8,409,807 | B2* | 4/2013 | Neely | G01R 33/302 435/6.12 |
| 9,409,955 | B2* | 8/2016 | Reguera | C07K 14/195 |
| 9,601,227 | B2* | 3/2017 | Reguera | H01B 1/12 |
| 10,647,780 | B2* | 5/2020 | Ewert | A61K 39/39566 |
| 2009/0089071 | A1* | 4/2009 | Doornebos | G06Q 20/12 705/342 |
| 2014/0129172 | A1 | 5/2014 | Eberhardt et al. | |

* cited by examiner

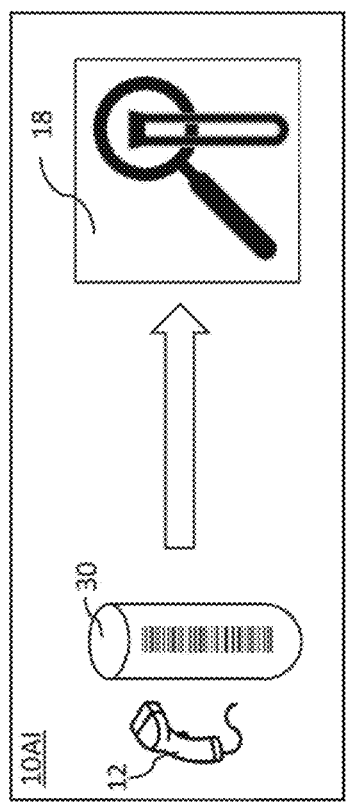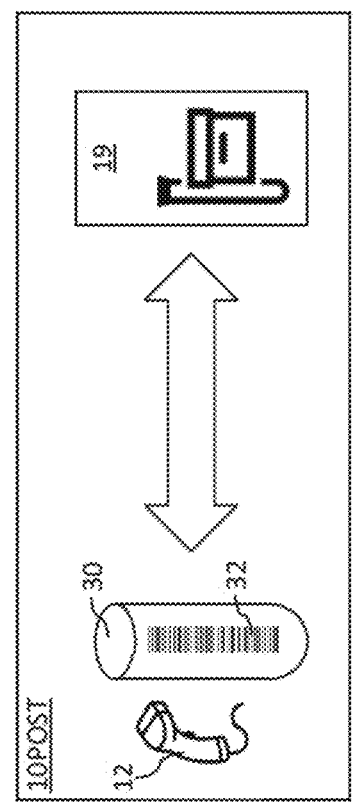

LABORATORY SYSTEM FOR ANALYZING BIOLOGICAL SAMPLES

CROSS-REFERENCE TO RELATED APPLICATIONS

This application claims priority to EP 18191546.3, filed Aug. 29, 2018, which is hereby incorporated by reference.

BACKGROUND

The present disclosure generally relates to a laboratory system for analyzing biological samples and a method for operating such a laboratory system.

In vitro diagnostic testing has a major effect on clinical decisions, providing physicians with pivotal information. In analytical laboratories, in particular clinical laboratories, a multitude of analyses on samples are executed by an analytical system in order to determine the physiological state of a patient.

In order to ensure healthcare professionals can rely on analytical test results for the diagnosis and treatment of patients, test result integrity is of utmost importance. A critical aspect of test result integrity is the association of the biological sample being tested to the right patient (whose sample it is). This is commonly achieved by associating a sample ID to each biological sample. In order to allow identification of a biological sample, the corresponding sample ID is commonly encoded into a barcode printed onto a label attached to a sample tube holding the biological sample, respectively attached onto a slide in case of tissue samples.

Since the sample ID is the only item allowing the association of analytical test results to the right patient, any error in processing of sample ID(s) has the potential to lead to a so-called sample mismatch. A sample mismatch is one of, if not the most serious adverse event in an analytical laboratory since it can lead to test result(s) being attributed to the wrong patient which can lead to false diagnosis/treatment of the patient. Therefore, state-of-the-art analytical laboratories implement various failsafe mechanisms to avoid and detect any error in identifying a sample.

Such failsafe mechanisms comprise the use of safe barcodes (barcodes which have some level of read-error tolerance and/or detection, such as checksum digits), repeat scanning of barcodes, and the like However, the stricter such failsafe mechanisms are set up, the higher the amount of manual labor is needed as anytime an error or even the slightest chance of an error is identified, the respective sample is flagged for manual error handling. On the other hand, less strict failsafe rules may result in read errors being undetected.

Furthermore, known methods of read error detection only allow detection of the instrument, respectively the identifier reader which could not read a sample identifier. However, since the sample identifier could not be read, it is not possible to determine which particular sample could not be identified. In automated laboratory systems, this could lead to situations where analytical tests ordered are skipped (not performed) if one of several instruments fails to identify the sample but the sample is then transported to the next instrument. The failure to identify the sample is overlooked and potentially critical analytical tests not performed. In some cases, the sample may be even contaminated if a more sensitive test is missed but followed by a less sensitive test.

Therefore, there is a need for a laboratory system and a method for operating such a laboratory system which allows for early detection of tag quality degradation and allows for the determination of the biological sample(s) which could not be identified by one or more of the laboratory instruments.

SUMMARY

According to the present disclosure, a laboratory system and method for analyzing biological samples are presented. The laboratory system can comprise a plurality of laboratory instruments. At least one of the plurality of laboratory instruments can be configured to receive and identify biological samples by reading a sample identifier ID from an identifier tag attached to a sample container holding the biological sample using an identifier tag reader. At least one of the plurality of laboratory instruments can be configured to transmit a processing order query to the laboratory control unit enquiring for a processing order indicative of one or more processing steps to be carried out on the biological sample. The query can comprise the sample identifier. At least one of the plurality of laboratory instruments can be configured to process the biological sample according to the processing order from the laboratory control unit. The laboratory system can also comprise a laboratory control unit communicatively connected to the plurality of laboratory instruments and a database. The laboratory control unit can be configured to transmit a processing order to querying laboratory instruments. The processing order can be generated based on one or more test orders in the database corresponding to the respective sample identifier ID. The laboratory control unit can also be configured to validate sequence of queries from the plurality of laboratory instruments against a valid query sequence pattern and to generate a warning/error signal if the sequence of queries from the plurality of laboratory instruments does not match the valid query sequence pattern. The warning/error signal can be indicative of at least one unsuccessful reading of the identifier tag by one of the plurality of laboratory instruments, thereby, identifying the particular sample whose identification failed.

Accordingly, it is a feature of the embodiments of the present disclosure to provide for a laboratory system and a method for operating such a laboratory system which allows for early detection of tag quality degradation and allows for the determination of the biological sample(s) which could not be identified by one or more of the laboratory instruments. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 7 illustrates a highly schematic block diagram of an embodiment of an analytical laboratory instrument of the disclosed laboratory system of the present disclosure.

FIG. 8 illustrates a highly schematic block diagram of an embodiment of a post-analytical laboratory instrument of the disclosed laboratory system of the present disclosure.

DETAILED DESCRIPTION

Figure 1:
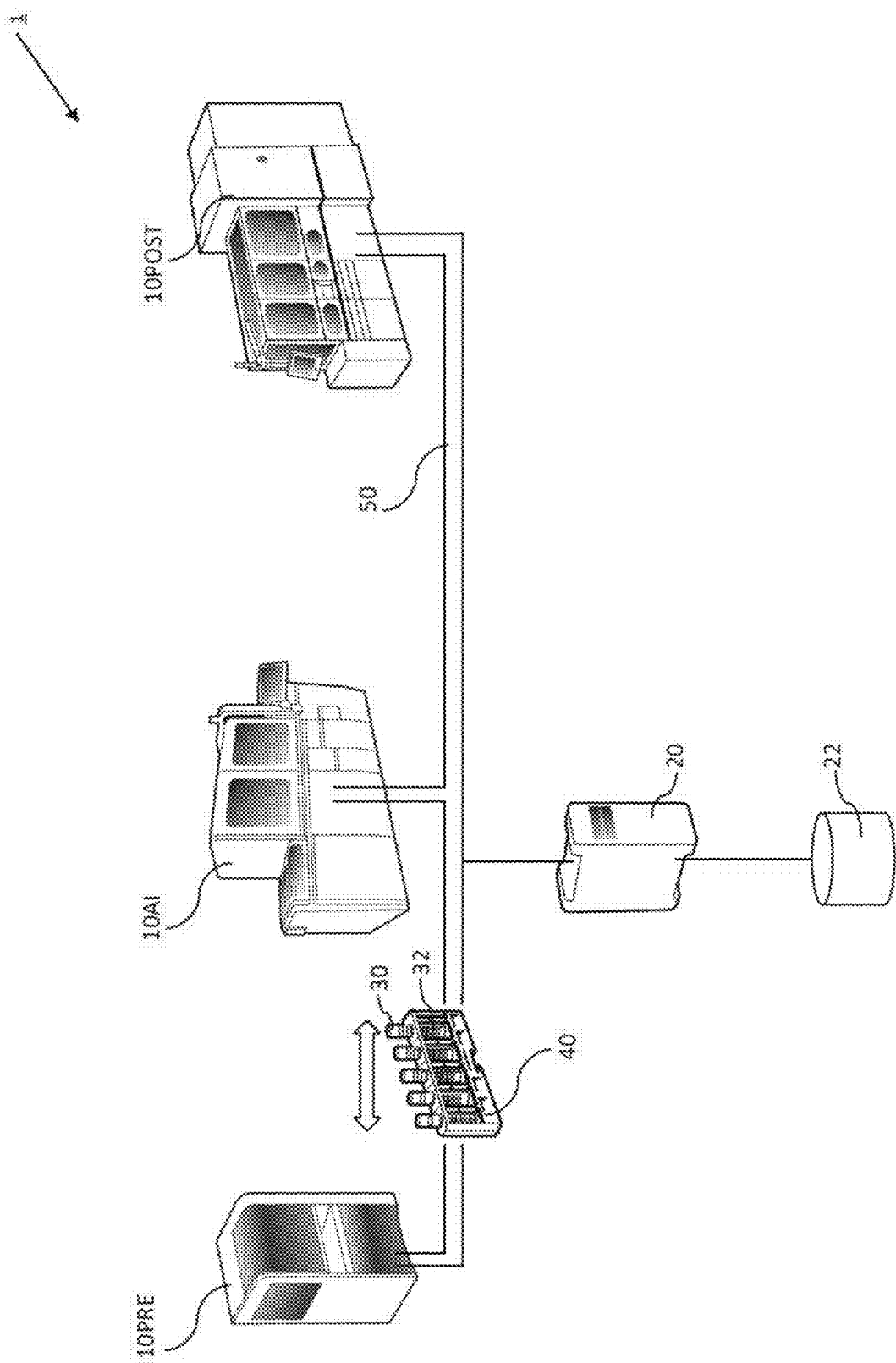
FIG. 1 illustrates highly schematic block diagram the disclosed laboratory system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Disclosed herein are a laboratory system for analyzing biological samples, a method for operating a laboratory system and, respectively, a computer program product for a control unit of a laboratory system which address the above-identified need by monitoring and validating a sequence of queries by laboratory instruments, queries related to processing steps to be performed on a biological sample received by the respective instrument.

The laboratory system disclosed herein can comprise a plurality of laboratory instruments communicatively connected to a control unit and a database. At least one of the plurality of laboratory instruments can be configured to receive and identify biological samples by reading a sample identifier ID from an identifier tag attached to a sample container holding the biological sample using an identifier tag reader. Furthermore, at least one of the plurality of laboratory instruments can be configured to transmit a processing order query to the laboratory control unit enquiring for a processing order indicative of one or more processing steps to be carried out on the biological sample. The query can comprise the sample identifier ID. Also, at least one of the plurality of laboratory instruments can be configured to process the biological sample according to the processing order from the laboratory control unit.

The laboratory control unit can be configured to transmit a processing order to querying laboratory instruments, the processing order being generated based on one or more test orders in the database corresponding to the respective sample identifier ID, to validate a sequence of queries from the plurality of laboratory instruments against a valid query sequence pattern, and to generate a warning/error signal if the sequence of queries from the plurality of laboratory instruments does not match the valid query sequence pattern, the warning/error signal being indicative of at least one unsuccessful reading of an identifier tag by one of the plurality of laboratory instruments.

Correspondingly, the disclosed method can comprise receiving and identify biological samples by reading a sample identifier ID from an identifier tag attached to a sample container holding the biological sample by one or more of a plurality of laboratory instruments using an identifier tag reader thereof and transmitting a processing order query by one or more of a plurality of laboratory instruments to the laboratory control unit enquiring for a processing order indicative of one or more processing steps to be carried out on the biological sample. The query can comprise the sample identifier ID. The method can also comprise transmitting a processing order by a laboratory control unit to querying laboratory instruments. The processing order can be generated based on one or more test orders in the database corresponding to the respective sample identifier ID. The method can also comprise validating a sequence of queries from the plurality of laboratory instruments against a valid query sequence pattern by the control unit and generate a warning/error signal if the sequence of queries from the plurality of laboratory instruments does not match the valid query sequence pattern. The warning/error signal can be indicative of at least one unsuccessful reading of an identifier tag by one of the plurality of laboratory instruments.

In other words, the sequence of query messages from the instruments can be monitored by the control unit and validated to check if there is a deviation from the expected sequence (pattern), which can be indicative that at least one instrument "missed" the identification of the sample.

The system and the method herein disclosed can be advantageous since, in addition to detecting that a sample identification error occurred, it can allow for the identification of the particular sample whose identification failed.

Additional embodiments disclosed herein further can comprise determining degradation of identifier tag reader(s) based on a sequence of two or more signals indicative of degrading tag quality and/or determining degradation of identifier tag writer(s) based on a sequence of two or more signals indicative of degrading tag quality and/or flagging analytical result(s) obtained by processing biological sample(s) held in sample container(s) if the tag quality corresponding to identifier tag(s) is below a critical tag quality threshold.

Such embodiments can be advantageous since they enable predicting upcoming failure(s) of tag reader(s) as well as writer(s)/supplier(s), thereby allowing predictive maintenance thereof to avoid further degradation and hence avoiding read errors. In addition, flagging of analytical result(s) corresponding to sample container(s) if the tag quality corresponding to identifier tag(s) is below a critical tag quality threshold can enable the review of such cases, thereby providing a higher level of certainty but at the same time avoiding complete discarding of valid analytical results (if the flagged results are released after being reviewed).

Being able to identify a degrading (faulty) identifier tag writer as well as a supplier of low quality identifier tags can be advantageous for root-cause analysis should a read error occur.

Certain terms will be used in this patent application, the formulation of which should not be interpreted to be limited by the specific term chosen but as to relate to the general concept behind the specific term.

The term 'laboratory instrument' as used herein can encompass any apparatus, or apparatus component, operable to execute one or more processing steps/workflow steps on one or more biological samples and/or one or more reagents. The expression 'processing steps' thereby can refer to physically executed processing steps such as centrifugation, aliquotation, sample analysis and the like. The term 'instrument' can cover pre-analytical instruments, post-analytical instruments and also analytical instruments.

The term 'pre-analytical instrument' as used herein can encompass any apparatus, or apparatus component, that can be configured to perform one or more pre-analytical processing steps/workflow steps comprising—but not limited to—centrifugation, resuspension (e.g., by mixing or vortexing), capping, decapping, recapping, sorting, tube type identification, sample quality determination and/or aliquotation steps. The processing steps may also comprise adding chemicals or buffers to a sample, concentrating a sample, incubating a sample, and the like.

The term 'analyzer'/'analytical instrument' as used herein can encompass any apparatus, or apparatus component, configured to obtain a measurement value. An analyzer can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectrometry of proteins or metabolites and physical or chemical parameters of various types. An analytical instrument may comprise units assisting with the pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow can be optimized for certain types of analysis. Examples of such analyzer can be clinical chemistry analyzers, coagulation chemistry analyzers, immunochemistry analyzers, urine analyzers, nucleic acid analyzers, used to detect the result of chemical or biological reactions or to monitor the progress of chemical or biological reactions. The term 'analyte' can be a component of a sample to be analyzed, e.g., molecules of various sizes, ions, proteins, metabolites and the like. Information gathered on an analyte may be used to evaluate the impact of the administration of drugs on the organism or on particular tissues or to make a diagnosis. Thus, 'analyte' can be a general term for substances for which information about presence and/or concentration is intended. Examples of analytes can be, for example, glucose, coagulation parameters, endogenic proteins (e.g., proteins released from the heart muscle), metabolites, nucleic acids and so on.

The term 'post-analytical instrument' as used herein can encompass any apparatus, or apparatus component, that can be configured to perform one or more post-analytical processing steps/workflow steps comprising—but not limited to—sample unloading, transport, recapping, decapping, temporary storage/buffering, archiving (refrigerated or not), retrieval and/or disposal.

The term 'communication network' as used herein can encompass any type of wireless network, such as, for example, a WIFI, GSM, UMTS or other wireless digital network or a cable based network, such as Ethernet or the like. In particular, the communication network can implement the Internet protocol (IP). For example, the communication network can comprise a combination of cable-based and wireless networks.

The term 'control unit' as used herein can encompass any physical or virtual processing device configurable to control a laboratory instrument/system comprising one or more laboratory instruments in a way that workflow(s) and workflow step(s) can be conducted by the laboratory instrument/system. The control unit may, for example, instruct the laboratory instrument/system to conduct pre-analytical, post analytical and analytical workflow(s)/workflow step(s). The control unit may receive information from a data management unit regarding which steps need to be performed with a certain sample. In some embodiments, the control unit might be integral with a data management unit, may be comprised by a server computer and/or be part of one laboratory instrument or even distributed across multiple instruments of the laboratory system. The control unit may, for instance, be embodied as a programmable logic controller running a computer-readable program provided with instructions to perform operations.

A 'data management unit' or 'database' can be a computing unit for storing and managing data. This may involve data relating to biological sample(s) to be processed by the automated system. The data management unit may be connected to an LIS (laboratory information system) and/or an HIS (hospital information system). The data management unit can be a unit within or co-located with a laboratory instrument. It may be part of the control unit. Alternatively, the database may be a unit remotely locater. For instance, it may be embodied in a computer connected via a communication network.

The terms 'sample', 'patient sample' and 'biological sample' can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample can be suspected to contain a certain antigen or nucleic acid.

The terms 'sample container' and 'sample tube' can refer to any individual container for storing, transporting, and/or processing a sample. In particular, the term without limitation can refer to a piece of laboratory glass- or plastic-ware, optionally comprising a cap on its upper end.

The term 'sample carrier' as used herein can refer to any kind of holder configured to receive one or more sample tubes and configured to be used for transporting sample tube(s). Sample carriers may be of two major types, single holders and sample racks. A 'single holder' can be a type of sample carrier configured to receive and transport a single sample tube. Typically, a single holder can be provided as a puck, i.e., a flat cylindrical object with an opening to receive and retain a single sample tube. A 'sample rack' can be a type of sample carrier, typically made of plastics and/or metal, adapted for receiving, holding and transporting sample tubes, e.g., 5 or more sample tubes e.g. disposed in one or more rows. Apertures, windows or slits may be present to enable visual or optical inspection or reading of the sample tubes or of the samples in the sample tubes or of a label, such as a barcode, present on the sample tubes held in the sample rack.

The term 'identification tag' as used herein can refer to an optical and/or radio frequency based identifier that can allow the identifier tag to be uniquely identified by a corresponding identification tag reader. The 'identification tag' can comprise—but is not limited to—a barcode, a QR code, or an RFID tag.

The term 'RFID tag' as used herein can refer to either an active or passive RFID tag that contains information. An RFID tag or transponder can include a coil or antenna and some information stored on an RFID chip that can be read and/or written by an RFID reader. Correspondingly, the RFID tag can be read only or read/write and the information associated with the RFID tag can be hard-coded into the RFID tag at the time of manufacture or at some later time.

The term 'RFID reader' as used herein can include devices that can read information from and/or write information into an RFID tag. Typically, RFID readers can include a coil or antenna and circuitry to transmit and receive signals with the coil or antenna. The RFID reader antenna can generate an electromagnetic field, thereby transferring energy to the tag. Depending on the design of the tag, a portion of the energy transferred to the tag can be reflected to the reader so as to provide information about the tag back to the reader. Some RFID systems can be used to read and optionally write data to and from the RFID tag. RFID readers can generate signals spanning distances from less than one centimeter to more than fifty meters depending on frequency and power of the signals generated at the RFID reader antenna.

A 'test order' as used herein can encompass any data object, computer loadable data structure, modulated data representing such data being indicative of one or more analytical tests to be executed on a particular biological sample. For example, a test order may be a file or an entry in a database. A test order can indicate an analytical test if, for example, the test order comprises or is stored in association with an identifier of an analytical test to be executed on a particular sample.

The term 'barcode quality' as used herein can refer to any data object indicative of the quality of a barcode. In particular, barcode quality can refer to the barcode quality as specified by the ISO/IEC International Standard 15416 for one-dimensional, respectively ISO/IEC 15415 for two-dimensional barcodes.

As shown on FIG. 1, the laboratory system 1 can comprise a plurality of laboratory instruments 10PRE, 10POST, 10AI, a laboratory control unit 20 communicatively connected to the plurality of laboratory instruments 10PRE, 10POST, 10AI, and a database 22.

At least one of the plurality of laboratory instruments 10PRE, 10POST, 10AI can be configured to receive and identify biological samples by reading the sample identifier ID from the identifier tag 32 attached to a sample container 30 holding the biological sample using an identifier tag reader. After having identified the biological sample, the laboratory instruments 10PRE, 10POST, 10AI can transmit a processing order query to the laboratory control unit 20 enquiring for a processing order indicative of one or more processing steps to be carried out on the biological sample, the query comprising the sample identifier ID. In other words, when an instrument receives a sample, it can "ask" the control unit what to do with that sample. After receiving back a processing order from the control unit 20, the laboratory instrument 10PRE, 10POST, 10AI can be configured to process the biological sample. Processing of a sample can comprise pre-analytical, analytical and post-analytical processing steps.

According to particular embodiments disclosed herein, the identifier tag(s) 32 can be a barcode, the identifier tag reader can be a barcode reader, and the identifier tag writer can be a barcode printer.

FIG. 1 shows a particular embodiment of the disclosed laboratory system 1 comprising a pre-analytical laboratory instrument 10PRE, an analytical laboratory instrument 10AI, a post-analytical laboratory instruments 10POST interconnected by a sample transportation system 50.

Specifics of the pre-analytical laboratory instrument 10PRE, analytical laboratory instruments 10AI, respectively post-analytical laboratory instruments 10POST will be described in detail with reference to FIGS. 5-8.

The sample transportation system 50, as its name suggests, can be configured to transport sample carrier(s) 40 holding one or more sample containers 30 from a first laboratory instrument 10PRE, 10POST, 10AI to a second laboratory instrument 10PRE, 10POST, 10AI of the plurality of laboratory instruments 10PRE, 10POST according to the data indicative of the next target instrument (and vice versa). According to embodiments disclosed herein, the sample transportation system 50 can be a one dimensional conveyor-belt based system, a two-dimensional transportation system (such as a magnetic sample carrier transport system), or a combination thereof.

Figure 2:
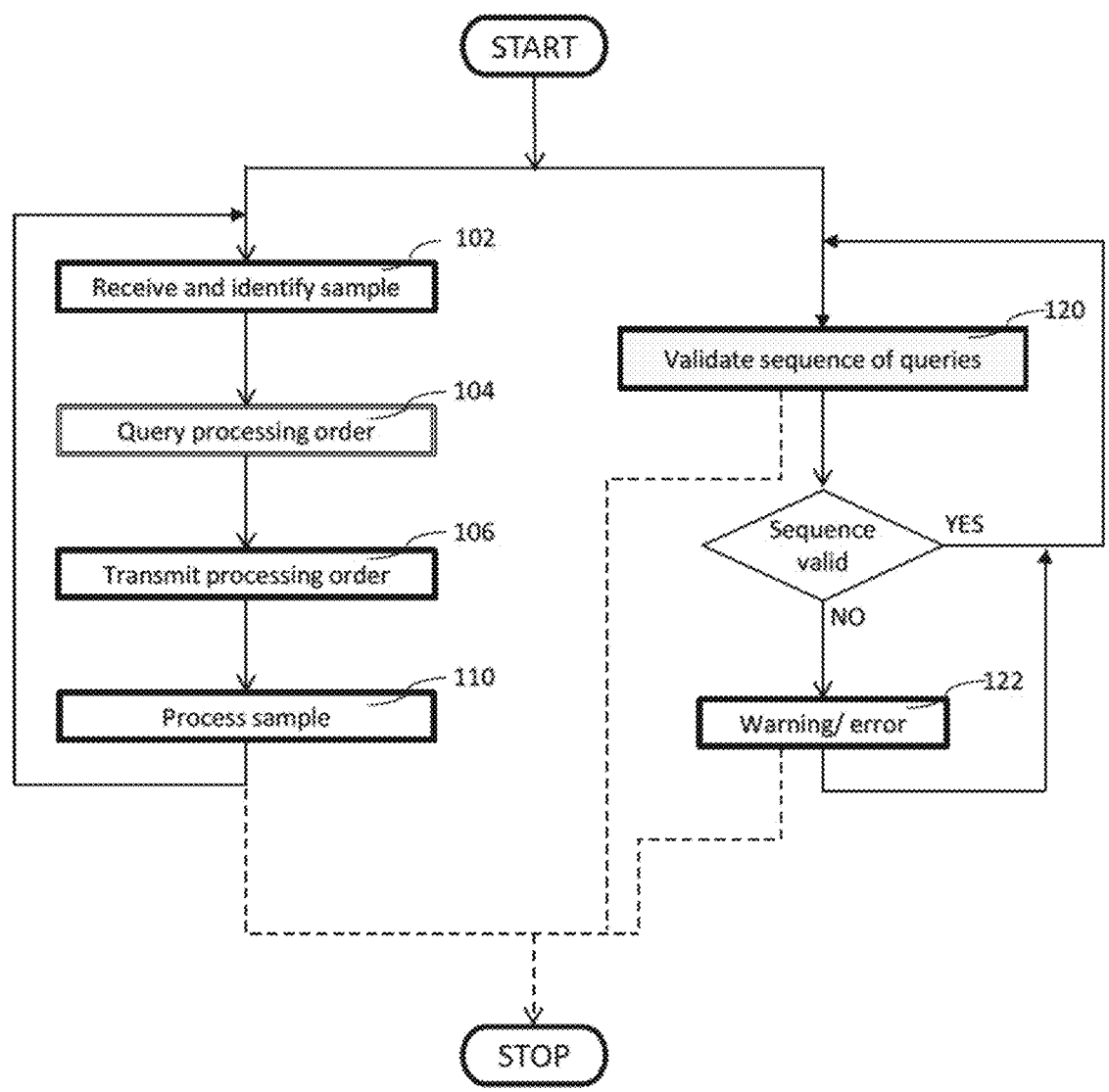
FIG. 2 illustrates a flowchart illustrating a first embodiment of the method of the present disclosure.

Turning now to FIG. 2, the functionality of the disclosed system, i.e., the steps of the disclosed method, will be described. In a step 102, the sample can be received and identified by one or more of the laboratory instruments 10PRE, 10POST, 10AI by an identifier tag reader 12 reading the sample identifier ID from an identifier tag 32 attached to a sample container 30 holding the biological sample. According to various embodiments disclosed herein, more than one, or even all laboratory instruments 10PRE, 10POST, 10AI can identify the biological sample. According to particular embodiments comprising an automated sample transportation system 50, only one instrument such as, for example, a pre-analytical laboratory instrument 10PRE may need to identify the biological sample, while all other laboratory instruments 10PRE, 10POST, 10AI can be notified by the control unit 20 as to which sample they are about to receive via the sample transportation system 50.

In step 104, the laboratory instruments 10PRE, 10POST, 10AI can send a processing order query to the control unit 20, enquiring about a processing order indicative of one or more processing steps to be carried out on the biological sample, the query comprising the sample identifier ID. In other words, the laboratory instruments 10PRE, 10POST, 10AI can ask the control unit 20 what to do with the sample they just identified. In response to being queried, in step 106, the laboratory control unit 20 can send back a processing order to querying laboratory instruments 10PRE, 10POST, 10AI, the processing order being generated based on one or more test orders in the database 22 corresponding to the respective sample identifier ID. In other words, the control unit 20 can check what test orders have been registered for the sample and can send corresponding test orders back to the querying instrument(s).

In subsequent step 1 the laboratory instruments 10PRE, 10POST, 10AI can process the biological sample(s) according to the processing order received from the control unit 20.

As illustrated on the flowchart of FIG. 2, the sequence of steps 102 through 110 can be repeated (depending on the particular sample processing workflow) a number of times by a plurality of laboratory instruments 10PRE, 10POST, 10AI. In step 120—parallel to the sequence of steps 102 through 110—the control unit 20 can validate the sequence of queries from the plurality of laboratory instruments 10PRE, 10POST, 10AI against a valid query sequence pattern. A sequence of queries can be considered to be valid if it correlates with the sample processing workflow of the biological sample in line with the test orders in the database 22.

If the sequence of queries from the plurality of laboratory instruments 10PRE, 10POST, 10AI does not match the valid query sequence pattern, in step 122, a warning/error signal can be generated by the control unit, wherein the warning/error signal can be indicative of at least one unsuccessful reading of the identifier tag 32 by one of the plurality of laboratory instruments 10PRE, 10POST, 10AI.

While using state of the art methods, it may not possible to tell which is the sample identifier that could not be read, according to further embodiments disclosed herein, the control unit 20 can be configured to identify the specific sample identifier(s) that could not be read by one or more analytical laboratory instruments 10AI by correlating the number of test query(s) received for each sample identifier with the number of test orders registered for the respective sample identifier(s) in order to avoid test orders staying open for extended periods of time. A test order can be open if no analytical laboratory instrument 10AI has processed the corresponding biological sample according to that test order. This can provide a significant advantage over known methods as manual intervention (e.g., to manually identify the sample container) can be greatly reduced. As an additional safety precaution, according to particular embodiments disclosed herein, test results corresponding to biological samples whose identifier could not be read by the laboratory instruments 10PRE, 10POST, 10AI—but deducted by control unit 20—can be flagged, so that a manual review can be performed and/or for audit trail reasons.

When the sequence of queries from the plurality of laboratory instruments 10PRE, 10POST, 10AI matches the valid query sequence pattern, the validation of the sequence of queries can continue.

Figure 3:
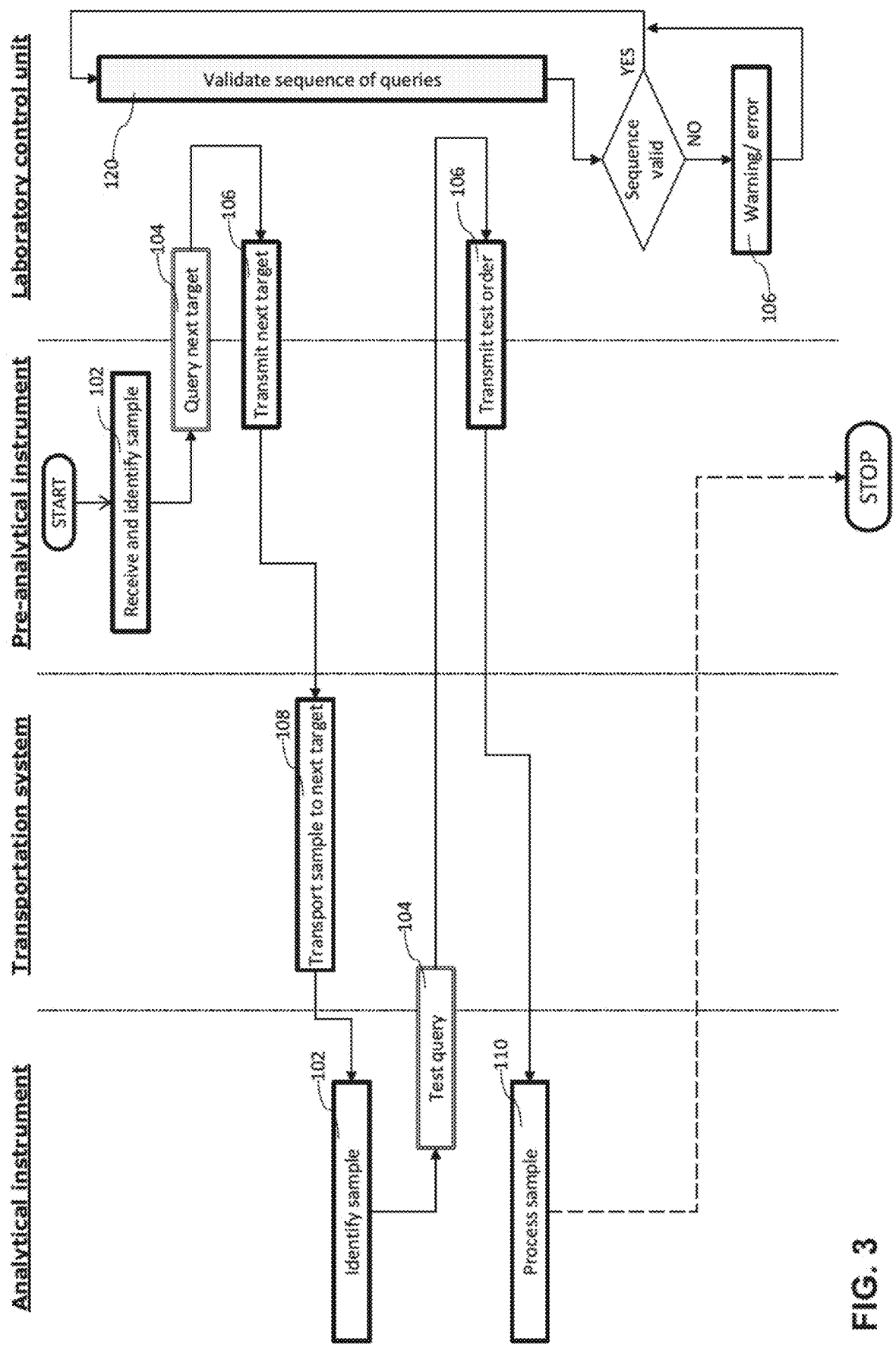
FIG. 3 illustrates a swim-lane diagram of an embodiment of the disclosed method of the present disclosure.

FIG. 3 shows a swim-lane diagram of a further embodiment of the disclosed method as carried out by a laboratory system 1 comprising at least one pre-analytical laboratory instrument 10PRE, an analytical laboratory instrument 10AI and a sample transportation system 50. In a first sequence of steps 102 to 1, a pre-analytical laboratory instrument 10PRE can receive a biological sample first, can prepare the sample, and can send the sample to an analytical laboratory instrument 10AI via the sample transportation system 50 according to a processing order comprising a next target instrument. In a second sequence of steps 102 to 1, the analytical laboratory instrument 10AI can receive and identify the biological sample, can send a test query to the control unit 20 in step 104 and can process the sample in step 110 according to the test order transmitted by the control unit 20 in step 106.

All this time (that is in parallel), the control unit 20 can monitor the queries from all instruments 10PRE, 10AI and validate the sequence of queries. In the example depicted in FIG. 3, the valid query sequence pattern can comprise the validity condition that a next target query must be followed by a test query. The absence of a test query following a next target query can be indicative of a failure to read the sample identifier ID from an identifier tag 32 by the next target analytical laboratory instrument 10AI identified in the next target query. In other words, if an instrument has queried for a next target instrument and then no query is received as to what test to be performed on the sample, then the conclusion may be drawn that the next target instrument could not identify the sample. Otherwise, the next target instrument would have asked what test to be done on it.

Figure 4:
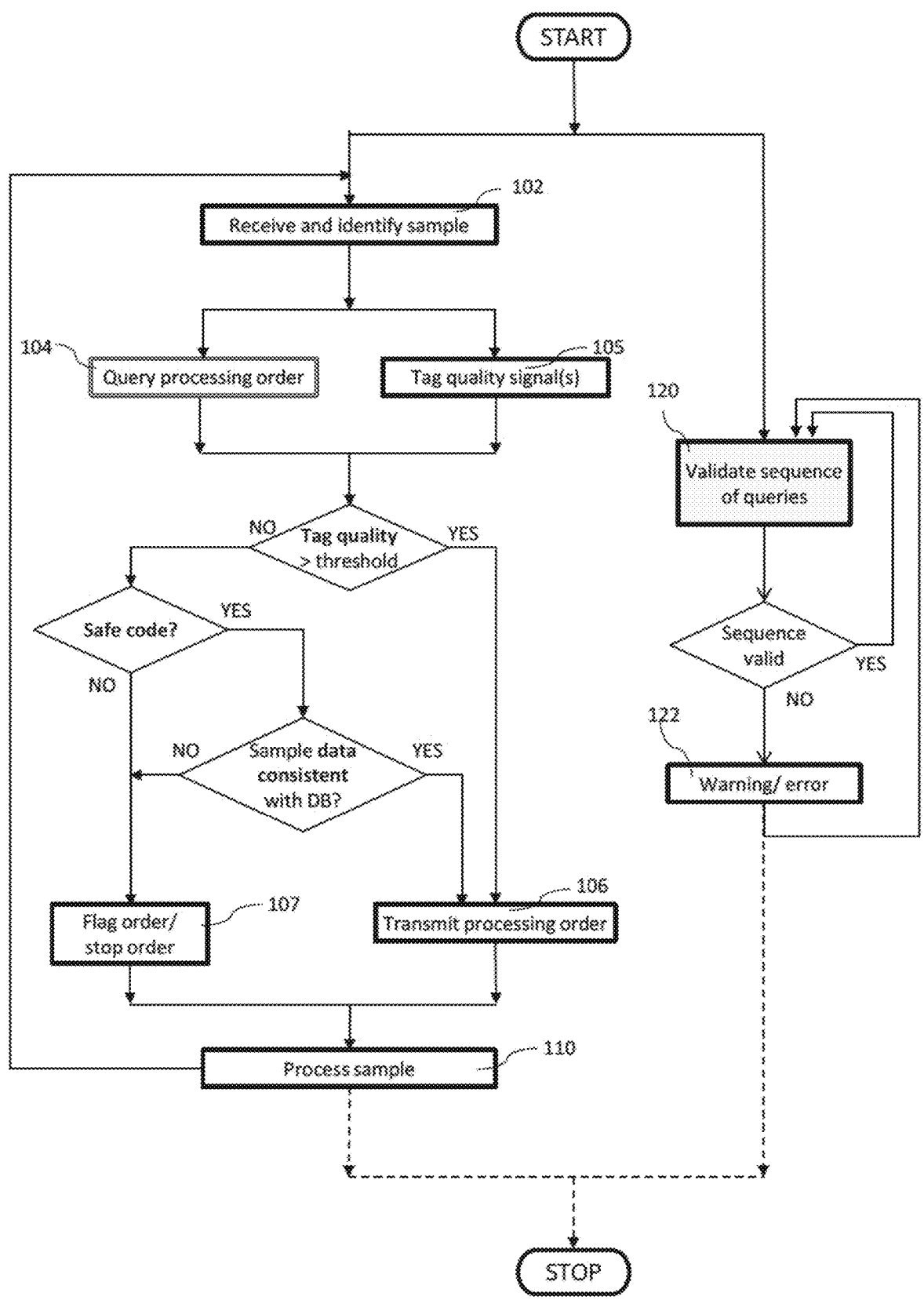
FIG. 4 illustrates a flowchart illustrating a further embodiment of the method disclosed herein of the present disclosure.

FIG. 4 shows a flowchart of a further embodiment disclosed wherein one or more of the plurality of laboratory instruments 10PRE, 10POST, 10AI—in a step 105—can transmit quality signal(s) to the laboratory control unit 20 indicative of a quality of the identifier tag 32 of sample container(s) by the identifier tag reader 12. In case of barcodes, for example, the quality signal(s) can be indicative of barcode quality as specified by the ISO/IEC International Standards 15415 and 15416. As illustrated on the flowchart, if the tag quality—based on the quality signal(s)—corresponding to identifier tag(s) 32 is below a critical tag quality threshold, the control unit 20 can only instruct the laboratory instrument 10PRE, 10POST, 10AI to process the biological sample if the sample identifier code on the identifier tag 32 is of a safe type and sample data read from the identifier tag 32 is consistent with sample data in the database 20. An identifier code can be of a safe type if the code implements a kind of fault tolerance such as, for example, a checksum. Data read from the identifier tag 32 can comprise (but is not limited to) the sample identifier ID, a sample type, sample collection date, and the like. This data can then be compared with corresponding data in the database. If the data read from the identifier tag 32 is consistent with the database 22, it can be safely concluded that no error occurred while reading the identifier tag 32—even though the quality signal from the identifier tag reader 12 indicated low label quality. On the other hand, if the tag quality corresponding to identifier tag(s) 32 is below a critical tag quality threshold and the sample identifier code on the identifier tag 12 is not of a safe type or the data read from the identifier tag 32 is not consistent with data in the database 20, the control unit 20 can instruct the laboratory instrument 10PRE, 10POST, 10AI to halt any processing of the biological sample in the sample container 30 with the respective identifier tag 32 and/or prompt a user to decide (e.g., by a user interface prompt, a configuration setting, and the like.) whether to halt or continue processing the biological sample(s) held in sample container(s) 30 with the respective identifier tag(s) 32 and/or instruct the laboratory instrument 10PRE, 10POST, 10AI to output the sample container 30 to an error position and/or flag analytical result(s) obtained by processing biological sample(s) held in sample container(s) 30 with the respective the identifier tag(s) 32 and/or create a log entry in the database 22 indicative of the tag quality, sample identifier ID and any data read from the identifier tag(s) 32.

Furthermore, relying on the tag quality signal(s) from the laboratory instruments 10PRE, 10POST, 10AI, the control unit 20 can determine degradation of an identifier tag reader 12 based on a sequence of two or more signals indicative of degrading tag quality, the sequence corresponding to readings of a plurality of identifier tags 32 by the same identifier tag reader 12. Furthermore, the control unit 20 can also be configured to determine degradation of an identifier tag writer 60 based on a sequence of two or more signals indicative of degrading tag quality, the sequence corresponding to readings of identifier tags 32 originating from one particular supplier and/or written by one particular identifier tag writer 60. Alternatively, or additionally, based on a sequence of two or more signals indicative of degrading tag quality, the control unit 20 can be configured to raise an alert that a certain supplier/source/provider of identifier tags 32 for sample containers 30 is providing low quality tags.

This can be advantageous in case of disputes over a cause of failed sample container identifications allowing a so-called root cause analysis, enabling the provider/operator of the laboratory instruments 10PRE, 10POST, 10AI to identify whether the fault lies with the identifier tags 32 or the identifier tag reader(s) 12. Additionally, the control unit 20 can be configured to determine if the tag quality corresponding to identifier tag(s) 32 is below a critical tag quality threshold and flag analytical result(s) obtained by processing biological sample(s) held in sample container(s) 30 with the respective the identifier tag(s) 32.

Turning now to FIGS. 5-8, particular embodiments of the laboratory instruments 10PRE, 10POST, 10AI are described.

Figure 5:
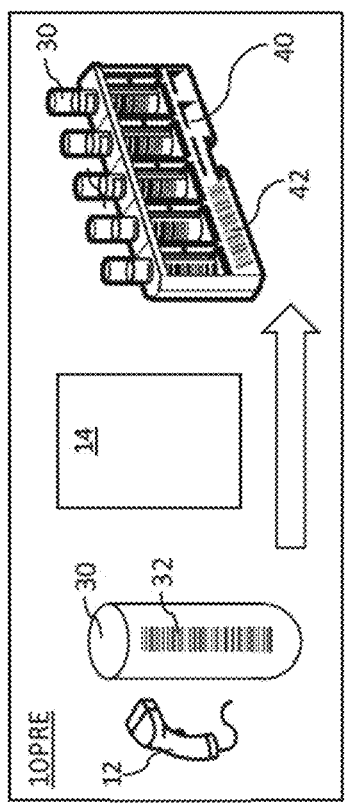
FIG. 5 illustrates a highly schematic block diagram of an embodiment of a pre-analytical laboratory instrument of the disclosed laboratory system of the present disclosure.

FIG. 5 shows a pre-analytical laboratory instrument 10PRE comprising a sample container sorting unit 14 configured to sort sample containers 30 holding biological samples into sample carriers 40, each sample carrier 40 being identified by a carrier identifier (Carrier-ID) of a carrier tag 42 attached to the sample carrier 40, the pre-analytical laboratory instruments 10PRE being further configured to transmit signals to the laboratory control unit associating the sample identifier(s) ID of sorted sample containers 30 with the sample carrier identifier(s) Carrier-ID of the corresponding sample carrier(s) 40.

For embodiments where a pre-analytical laboratory instrument 10PRE sorts sample containers 30 into sample carriers 40, one or more analytical laboratory instruments 10AI can be further configured to read the carrier identifier Carrier-ID from the carrier tag 42 and transmit the carrier identifier Carrier-ID to the laboratory control unit 20 with the test query. Correspondingly, the laboratory control unit 20 can be configured to generate a warning/error signal if the carrier identifier Carrier-ID and sample identifier ID of a test query does not match the association by the pre-analytical laboratory instruments 10PRE upon sorting. In this way, sorting and/or handling errors of the sample carriers 40 can be identified.

For pre-analytical laboratory instruments 10PRE, the query by pre-analytical laboratory instrument(s) 10PRE to the laboratory control unit 20 for a processing order can comprise a next target query. Correspondingly, when queried by a pre-analytical laboratory instrument 10PRE, the control unit 20 can be configured to transmit data indicative of a next target instrument for the biological sample based on its sample identifier ID and the list of test orders.

Figure 6:
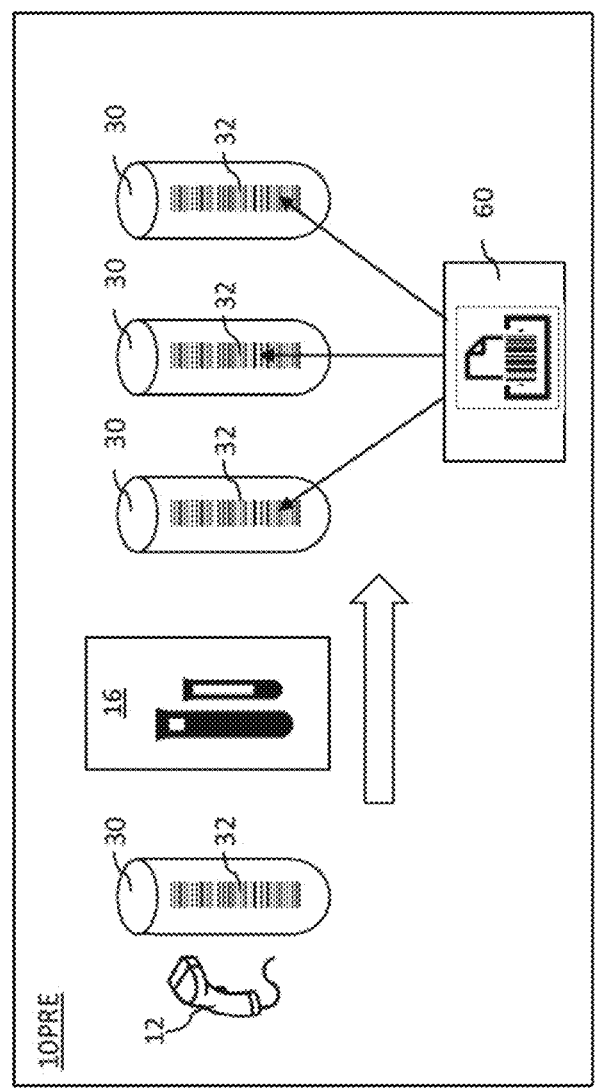
FIG. 6 illustrates a highly schematic block diagram of a further embodiment of a pre-analytical laboratory instrument of the disclosed laboratory system of the present disclosure.

FIG. 6 shows a further embodiment of a pre-analytical laboratory instrument 10PRE, comprising an aliquoting unit 16 configured to prepare aliquots of biological sample(s) from the sample container(s) 30 and provide each of the aliquots with a sample identifier ID on an identifier tag 32 by an identifier tag writer 60. Correspondingly, the control unit can be configured to determine degradation of the identifier tag writer 60 of the pre-analytical laboratory instrument 10PRE based on a sequence of two or more signals indicative of degrading tag quality, the sequence corresponding to readings of identifier tags 32 of aliquots originating from this particular pre-analytical laboratory instrument 10PRE.

FIG. 7 shows an embodiment of an analytical laboratory instrument 10AI, comprising an analytical unit 18 configured to carry out an analytical test to measure the presence and/or concentration of at least one analyte in the biological sample. The query by the analytical laboratory instruments 10AI to the laboratory control unit 20 for a processing order can comprise a test query as to which analytical test(s) to carry out on the biological sample based on its sample identifier ID. Correspondingly, the laboratory control unit 20 can be configured to retrieve a list of test orders from the database based on the sample identifier ID, the list of test orders comprising one or more test orders, each test order being indicative of one or more processing steps to be carried out on the biological sample. When queried by an analytical instrument 10AI and having retrieved the list of test orders, the control unit 20 can transmit the test orders to the querying analytical instrument 10AI based on the sample identifier ID. The analytical laboratory instrument 10AI can then perform an analytical test of the biological sample in response to the test orders.

FIG. 8 shows an embodiment of a post-analytical laboratory instrument 10POST comprising a storage unit 19. The post-analytical laboratory instrument 10AI can be configured to store respectively retrieve sample containers 30 into respectively from the storage unit 19. The query by post-analytical laboratory instrument(s) 10POST to the laboratory control unit for a processing order can comprise a container to store respectively retrieve into respectively from the storage unit 19. Correspondingly, when queried by a post-analytical laboratory instrument 10POST, the control unit 20 can transmit data indicative of a sample container 30 to be retrieved from the storage unit 19. In response to the data indicative of a sample container 30 to be stored respectively retrieved, the post-analytical laboratory instrument 10POST can store and retrieve the sample container 30 from the storage unit 19.

For post-analytical laboratory instruments 10POST, the valid query sequence pattern can comprise a validity condition that a container to retrieve query must be followed by a test query. The absence of a test query following a container to retrieve query can be indicative of a failure to read the sample identifier ID from an identifier tag 32 by one of the laboratory instruments 10PRE, 10POST, 10AI. In other words, knowing that a sample container 30 can be retrieved from the post-analytical laboratory instrument 10POST for an analytical test to be performed, the control unit can deduct that an analytical instrument 10AI could not identify the sample if no test query is received.

Further disclosed and proposed is a computer program product including computer-executable instructions for performing the disclosed method in one or more of the embodiments enclosed herein when the program is executed on a computer or computer network. Specifically, the computer program may be stored on a computer-readable data carrier or a server computer. Thus, specifically, one, more than one or even all of method steps as indicated above may be performed by using a computer or a computer network, preferably by using a computer program.

As used herein, a computer program product refers to the program as a tradable product. The product may generally exist in any format, such as in a paper format, or on a computer-readable data carrier on premise or located at a remote location. Specifically, the computer program product may be distributed over a data network (such as a cloud environment). Furthermore, not only the computer program product, but also the execution hardware may be located on premise or in a cloud environment.

Further disclosed and proposed is a computer-readable medium comprising instructions which, when executed by a computer system, cause a laboratory system to perform the method according to one or more of the embodiments disclosed herein.

Further disclosed and proposed is a modulated data signal comprising instructions which, when executed by a computer system, cause a laboratory system to perform the method according to one or more of the embodiments disclosed herein.

Referring to the computer-implemented aspects of the disclosed method, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory system for analyzing biological samples, the laboratory system comprising:
   a plurality of laboratory instruments, wherein at least one of the plurality of laboratory instruments is configured to receive and identify biological samples by reading a sample identifier ID from an identifier tag attached to a sample container holding the biological sample using an identifier tag reader, wherein at least one of the plurality of laboratory instruments is configured to transmit a processing order query to a laboratory control unit enquiring for a processing order indicative of one or more processing steps to be carried out on the biological sample, the query comprising the sample identifier, and wherein at least one of the plurality of laboratory instruments is configured to process the biological sample according to the processing order from the laboratory control unit; and
   wherein the laboratory control unit is communicatively connected to the plurality of laboratory instruments and a database, the laboratory control unit being configured to:
      transmit a processing order to querying laboratory instruments, the processing order being generated based on one or more test orders in the database corresponding to the respective sample identifier ID,
      validate sequence of queries from the plurality of laboratory instruments against a valid query sequence pattern, and
      generate a warning/error signal if the sequence of queries from the plurality of laboratory instruments does not match the valid query sequence pattern, the warning/error signal being indicative of at least one unsuccessful reading of the identifier tag by one of the plurality of laboratory instruments, thereby identifying the particular sample whose identification failed.

2. The laboratory system for analyzing biological samples according to claim 1, wherein the valid query sequence pattern comprises a validity condition that a next target query must be followed by a test query, wherein the absence of a test query following the next target query is indicative of a failure to read the sample identifier ID from an identifier tag by a next target analytical laboratory instrument identified in the next target query and/or the valid query sequence pattern comprises a validity condition that a container to retrieve query must be followed by a test query, wherein the absence of a test query following a container to retrieve query is indicative of a failure to read the sample identifier ID from an identifier tag by one of the laboratory instruments.

3. The laboratory system for analyzing biological samples according to claim 1, wherein the plurality of laboratory instruments comprises one or more pre-analytical instruments, wherein the query by the pre-analytical laboratory instrument(s) to the laboratory control unit for a processing order comprises a next target query, and/or one or more analytical laboratory instruments comprising an analytical unit configured to carry out an analytical test to measure the presence and/or concentration of at least one analyte in the biological sample, wherein the query by the analytical laboratory instruments to the laboratory control unit for a processing order comprises a test query as to which analytical test(s) to carry out on the biological sample based on its sample identifier ID, and/or one or more post-analytical laboratory instruments, comprising a storage unit, the post-analytical laboratory instruments being configured to store respectively retrieve sample containers into respectively from the storage unit, wherein the query by post-analytical laboratory instrument(s) to the laboratory control unit for a processing order comprises a container to store respectively retrieve into respectively from the storage unit.

4. The laboratory system for analyzing biological samples according to claim 3, wherein the laboratory control unit is configured to retrieve a list of test orders from the database based on the sample identifier ID, the list of test orders comprising one or more test orders, each test order being indicative of one or more processing steps to be carried out on the biological sample, to transmit, when queried by an analytical instrument, test orders to the querying analytical instrument based on the sample identifier ID, to transmit, when queried by a pre-analytical laboratory instrument, data indicative of a next target instrument for the biological sample based on its sample identifier ID and the list of test orders and to transmit, when queried by a post-analytical laboratory instruments, data indicative of a sample container to be retrieved from the storage unit.

5. The laboratory system for analyzing biological samples according to claim 3, further comprising:
   a sample transportation system configured to transport sample carrier(s) from a first laboratory instrument of the plurality of laboratory instruments to a second laboratory instrument of the plurality of laboratory instruments according to data indicative of the next target instrument.

6. The laboratory system for analyzing biological samples according to claim 3, wherein the one or more pre-analytical laboratory instruments comprise a sample container sorting unit configured to sort sample containers holding biological samples into sample carriers, each sample carrier being identified by a carrier identifier (Carrier-ID) of a carrier tag attached to the sample carrier, wherein the pre-analytical laboratory instruments is configured to transmit signals to the laboratory control unit associating the sample identifier(s) of sorted sample containers with the sample carrier identifier(s) (Carrier-ID) of the corresponding sample carrier(s) and/or the one or more pre-analytical laboratory instruments comprise an aliquoting unit configured to prepare aliquots of biological sample(s) from the sample container(s) and provide each of the aliquots with a sample identifier ID on an identifier tag by an identifier tag writer.

7. The laboratory system for analyzing biological samples according to claim 6, wherein one or more analytical laboratory instruments are configured to read the carrier identifier (Carrier-ID) from the carrier tag and transmit the carrier identifier (Carrier-ID) to the laboratory control unit with the test query and/or the laboratory control unit is configured to generate a warning/error signal if the carrier identifier (Carrier-ID) and sample identifier ID of a test query does not match the association by the pre-analytical laboratory instruments upon sorting.

8. The laboratory system for analyzing biological samples according to claim 1, wherein the laboratory control unit is configured to identify a sample identifier(s) that could not be read by one or more analytical laboratory instruments by correlating the number of test query(s) received for each sample identifier with the number of test orders registered for the respective sample identifier(s) in order to avoid test orders staying open for extended periods of time, wherein a test order is open if no analytical laboratory instrument has processed the corresponding biological sample according to that test order.

9. The laboratory system for analyzing biological samples according to claim 1, wherein one or more of the plurality of laboratory instruments is configured to transmit quality signal(s) to the laboratory control unit indicative of a quality of the identifier tag of sample container(s) by the identifier tag reader.

10. The laboratory system for analyzing biological samples according to claim 9, wherein the laboratory control unit is configured to:
   determine degradation of an identifier tag reader based on a sequence of two or more signals indicative of degrading tag quality, the sequence corresponding to readings of a plurality of identifier tags by the same identifier tag reader; and/or
   determine degradation of an identifier tag writer based on a sequence of two or more signals indicative of degrading tag quality, the sequence corresponding to readings of identifier tags originating from one particular supplier and/or written by one particular identifier tag writer; and/or
   determine if the tag quality corresponding to identifier tag(s) is below a critical tag quality threshold and flag analytical result(s) obtained by processing biological sample(s) held in sample container(s) with the respective the identifier tag(s).

11. The laboratory system for analyzing biological samples according to claim 9, wherein the laboratory control unit is configured to:
   instruct the laboratory instrument to process the biological sample in the sample container with the respective identifier tag according to the processing order transmitted to the laboratory instrument, if the tag quality, based on the quality signal(s), corresponding to identifier tag(s) is above a critical tag quality threshold or the identifier tag comprises a sample identifier code of a safe type and data read from the identifier tag is consistent with data in the database,
   instruct the laboratory instrument to halt any processing of the biological sample and/or prompt a user to decide whether to halt or continue processing the biological sample(s) held in sample container(s) with the respective the identifier tag(s) and/or output the sample container to an error position and/or flag analytical result(s) obtained by processing the biological sample(s) held in sample container(s) with the respective the identifier tag(s), if the tag quality, based on the quality signal(s), corresponding to identifier tag(s) is below a critical tag quality threshold and the identifier tag does not comprise a sample identifier code of a safe type or the data read from the identifier tag is not consistent with data in the database.

12. A method for operating a laboratory system for analyzing biological samples, the method comprising:
   receiving and identify biological samples by reading a sample identifier ID from an identifier tag attached to a sample container holding the biological sample by one or more of a plurality of laboratory instruments using an identifier tag reader thereof;
   transmitting a processing order query by one or more of a plurality of laboratory instruments to a laboratory control unit enquiring for a processing order indicative of one or more processing steps to be carried out on the biological sample, the query comprising the sample identifier ID;
   transmitting a processing order by the laboratory control unit to querying laboratory instruments, the processing order being generated based on one or more test orders in the database corresponding to the respective sample identifier ID;
   processing the biological sample according to the processing order from the laboratory control unit by at least one of the plurality of laboratory instruments; and
   validating a sequence of queries from the plurality of laboratory instruments against a valid query sequence pattern by the laboratory control unit and generate a warning/error signal if the sequence of queries from the plurality of laboratory instruments does not match the valid query sequence pattern, the warning/error signal being indicative of at least one unsuccessful reading of an identifier tag by one of the plurality of laboratory instruments, thereby identifying the particular sample whose identification failed.

13. The method according to claim 12, further comprising [H]:
   querying the control unit by one or more pre-analytical laboratory instruments for a next target instrument for biological samples;
   when queried by a pre-analytical laboratory instrument, transmitting data indicative of a next target instrument for the biological sample based on its sample identifier ID by the laboratory control unit;
   transporting a sample carrier(s) holding a sample container from a first laboratory instrument to a second laboratory of the plurality of laboratory instruments by a sample transportation system according to data indicative of the next target instrument;
   querying the laboratory control unit by one or more analytical laboratory instruments as to which analytical test(s) to carry out on the biological sample based on its sample identifier ID;
   when queried by an analytical instrument, transmitting test orders by the control unit to the plurality of analytical instruments based on the sample identifier ID and the querying analytical instrument;

performing an analytical test of the biological sample by one or more analytical laboratory instruments in response to the test orders;

querying the laboratory control unit by one or more post-analytical laboratory instruments as to a container to retrieve;

when queried by a post-analytical laboratory instruments, transmitting data indicative of a sample container by the control unit to be stored respectively retrieved from the storage unit; and storing respectively retrieving a sample container from the storage unit of a post-analytical laboratory instruments according to the data indicative of a sample container to be stored respectively retrieved from the storage unit.

14. The method according to claim 13, further comprising:

identifying a sample identifier(s) that could not be read by one or more analytical laboratory instruments by correlating the number of test query(s) received for each sample identifier with the number of test orders registered for the respective sample identifier(s) in order to avoid test orders staying open for extended periods of time, wherein a test order is open if no analytical laboratory instrument has processed the corresponding biological sample according to that test order.

15. The method according to one of the claim 12, further comprising:

transmitting by one or more of the plurality of laboratory instruments tag quality signal(s) to the laboratory control unit indicative of a tag quality of the identifier tag of sample container(s) by the identifier tag reader.

* * * * *